US012746016B2

(12) United States Patent
Fleischli et al.

(10) Patent No.: US 12,746,016 B2
(45) Date of Patent: Sep. 29, 2026

(54) ACL DRILL GUIDE ASSEMBLY

(71) Applicant: Reconstruct Medical Supply LLC, Charlotte, NC (US)

(72) Inventors: James Fleischli, Charlotte, NC (US); Kemp R. Dunaway, Charlotte, NC (US); Trevor Lewis, Charlotte, NC (US)

(73) Assignee: Reconstruct Medical Supply LLC, Charlotte, NC (US)

( * ) Notice: Subject to any disclaimer, the term of this patent is extended or adjusted under 35 U.S.C. 154(b) by 82 days.

(21) Appl. No.: 18/792,672

(22) Filed: Aug. 2, 2024

(65) Prior Publication Data

US 2025/0040943 A1 Feb. 6, 2025

Related U.S. Application Data

(60) Provisional application No. 63/530,723, filed on Aug. 4, 2023.

(51) Int. Cl.
*A61B 17/17* (2006.01)

(52) U.S. Cl.
CPC ...... *A61B 17/1714* (2013.01); *A61B 17/1764* (2013.01)

(58) Field of Classification Search
CPC ............ A61B 17/1714; A61B 17/1764; A61B 17/8872; A61B 17/1796; A61B 17/8897
USPC ..................... 606/96–98, 79–80, 87–88, 103
See application file for complete search history.

(56) References Cited

U.S. PATENT DOCUMENTS

| | | | | | |
|---|---|---|---|---|---|
| 4,257,411 | A * | 3/1981 | Cho | A61B 17/1714 | 606/96 |
| 5,112,337 | A * | 5/1992 | Paulos | A61B 17/1764 | 606/98 |
| 5,163,940 | A * | 11/1992 | Bourque | A61B 17/1764 | 606/88 |
| 5,320,115 | A * | 6/1994 | Kenna | A61B 17/1764 | 128/898 |
| 5,320,626 | A * | 6/1994 | Schmieding | A61B 17/1714 | 606/96 |
| 5,601,550 | A * | 2/1997 | Esser | A61B 17/6433 | 606/54 |
| 5,603,716 | A * | 2/1997 | Morgan | A61B 17/1714 | 606/88 |
| 5,968,050 | A * | 10/1999 | Torrie | A61B 17/1714 | 606/86 R |
| 6,074,392 | A * | 6/2000 | Durham | A61B 17/1717 | 606/62 |

(Continued)

*Primary Examiner* — Jessica Weiss
(74) *Attorney, Agent, or Firm* — Clements Bernard Walker; Christopher L. Bernard

(57) ABSTRACT

An ACL drill guide assembly for use in an ACL or similar surgical procedure. The drill guide assembly is sterilizable and reusable, and includes an engagement end that includes a tongue structure and serrated teeth that are adapted to securely engage the back of the condyle of the knee and provide proper angled orientation for subsequent guide pin/drill placement and use. The shaft of the drill guide assembly is movable/rotatable such that the same drill guide assembly may be used for both left-side and right-side procedures. Labeling is provided on the drill guide assembly for conveniently indicating the associated tunnel diameter and offset from the engaged bone surface. Further, the handle and shaft may be disengaged via a convenient locking mechanism.

10 Claims, 13 Drawing Sheets

(56) References Cited

U.S. PATENT DOCUMENTS 6,120,511 A * 9/2000 Chan .................. A61B 17/1637 606/179
6,238,404 B1 * 5/2001 Hidalgo ............. A61B 17/0482 606/144
6,254,605 B1 * 7/2001 Howell .............. A61B 17/1764 606/86 R
6,419,678 B1 * 7/2002 Asfora ............... A61B 17/1757 606/96
D574,495 S * 8/2008 Petersen ...................... D24/140
8,439,947 B2 * 5/2013 Howard ............. A61B 17/1684 606/232
9,289,223 B2 * 3/2016 Piasecki ............. A61B 17/8872
10,070,874 B2 * 9/2018 Laviano ............. A61B 17/1631
10,123,812 B1 * 11/2018 Alvarado ........... A61B 17/1675
10,945,744 B2 * 3/2021 Ponzer ............... A61B 17/1728
2002/0055783 A1 * 5/2002 Tallarida ............ A61B 17/1764 623/20.14
2005/0038444 A1 * 2/2005 Binder, Jr. ......... A61B 17/1728 606/96
2005/0177171 A1 * 8/2005 Wetzler .................. A61B 17/17 606/96
2006/0106399 A1 * 5/2006 Taras ..................... A61B 17/17 606/96
2009/0149858 A1 * 6/2009 Fanelli ............... A61B 17/1764 606/80
2009/0228012 A1 * 9/2009 Gangji ............... A61B 17/3472 606/80
2011/0208194 A1 * 8/2011 Steiner ............... A61B 17/1637 606/80
2011/0313478 A1 * 12/2011 Herdrich ............ A61B 17/1764 606/86 R
2012/0197259 A1 * 8/2012 Smith ................ A61B 17/1764 606/88
2012/0265205 A1 * 10/2012 Steiner ............... A61B 17/1764 606/80
2014/0276884 A1 * 9/2014 Lizardi .................. A61B 90/00 606/102
2014/0316414 A1 * 10/2014 Steiner ............... A61B 17/1631 606/80
2015/0127012 A1 * 5/2015 Pilgeram ............ A61B 17/1714 606/88
2016/0089161 A1 * 3/2016 Ardito ................ A61B 17/1714
2018/0049755 A1 * 2/2018 Laviano ............. A61B 17/1714
2019/0015114 A1 * 1/2019 Fernandez ......... A61B 17/1725
2019/0105064 A1 * 4/2019 Ponzer ............... A61B 17/1728
2019/0231370 A1 * 8/2019 Muser .................... A61B 17/17
2019/0274697 A1 * 9/2019 Santangelo ........ A61B 17/1764
2021/0015503 A1 * 1/2021 Arciero .............. A61B 17/1796

* cited by examiner

ACL DRILL GUIDE ASSEMBLY

CROSS-REFERENCE TO RELATED APPLICATION

The present disclosure claims the benefit of priority of U.S. Provisional Patent Application No. 63/530,723, filed on Aug. 4, 2023, and entitled "ACL DRILL GUIDE ASSEMBLY," the contents of which are incorporated in full by reference.

TECHNICAL FIELD

The present disclosure relates generally to the minimally invasive surgery (MIS) field. More particularly, the present disclosure relates to an anterior cruciate ligament (ACL) drill guide assembly for use in an ACL or similar surgical procedure.

BACKGROUND

In MIS procedures, it is common for a surgeon to first place a drill guide through the skin and musculature and engage a bone site where a hole or tunnel is to be drilled for subsequent anchor or implant placement or tissue connection. A guide pin is disposed through this drill guide and engaged with the bone site, such that a solid or flexible drill can then be guided to the bone site, through the drill guide and/or around the guide pin. When using such a drill guide, it is often desirable that the engagement end of the drill guide be disposed at an angle to a handle of the drill guide, making use easier and more effective. This is true in both left-side and right-side procedures, which typically require that different drill guides be used.

The present background is provided as illustrative environmental context only and should not be construed to be limiting in any manner. The concepts and principles of the present disclosure may be implemented in other contexts as well, without limitation. For example, any MIS procedure can be addressed by the present disclosure, not merely ACL procedures.

SUMMARY

The present disclosure provides an ACL drill guide assembly for use in an ACL or similar surgical procedure. The drill guide assembly is sterilizable and reusable, and includes an engagement end that includes a tongue structure and serrated teeth that are adapted to securely engage the back of the condyle of the knee or other anatomical structure and provide proper angled orientation for subsequent guide pin/drill placement and use. The shaft of the drill guide assembly is movable/rotatable such that the same drill guide assembly may be used for both left-side and right-side procedures. Labeling is provided on the drill guide assembly for conveniently indicating the associated tunnel diameter and offset from the engaged bone surface. Further, the handle and shaft may be disengaged via a convenient locking mechanism.

In some embodiments, the present disclosure provides a drill guide assembly including: a handle assembly and a shaft assembly removably and securably coupled to the handle assembly, where the shaft assembly includes a foot structure including a tongue structure and serrated teeth that are adapted to securely engage a back of a condyle of a knee of a patient and provide proper angled orientation for subsequent guide pin/drill placement and use through the handle assembly and shaft assembly. A channel defined by the foot structure is disposed at an inclination angle relative to the shaft assembly. The channel defined by the foot structure is disposed at a left-side or right-side rotation angle relative to the handle assembly. In some embodiments, the handle assembly includes a ball seal and the shaft assembly includes a ball seal adapter by which the shaft assembly is removably coupled to the handle assembly. In some embodiments, the handle assembly includes a locking knob and constriction screw by which the shaft assembly is securably coupled to the handle assembly. In some embodiments, the foot structure includes a label indicating an associated tunnel diameter of the shaft assembly and offset of the foot structure from an engaged bone surface. In some embodiments, the shaft assembly includes an indicia indicating an associated left-side or right-side configuration of the shaft assembly with respect to the handle assembly. In some embodiments, the shaft assembly is freely rotatable relative to the handle assembly prior to being secured to the handle assembly. In some embodiments, the shaft assembly is rotatable relative to the handle assembly in a plurality of keyed detent positions prior to being secured to the handle assembly.

In some embodiments, the present disclosure provides a drill guide method including: providing a handle assembly and coupling a removable and securable shaft assembly to the handle assembly, where the shaft assembly includes a foot structure including a tongue structure and serrated teeth that are adapted to securely engage a back of a condyle of a knee of a patient and provide proper angled orientation for subsequent guide pin/drill placement and use through the handle assembly and shaft assembly. A channel defined by the foot structure is disposed at an inclination angle relative to the shaft assembly. The channel defined by the foot structure is disposed at a left-side or right-side rotation angle relative to the handle assembly. In some embodiments, the handle assembly includes a ball seal and the shaft assembly includes a ball seal adapter by which the shaft assembly is removably coupled to the handle assembly. In some embodiments, the handle assembly includes a locking knob and constriction screw by which the shaft assembly is securably coupled to the handle assembly. In some embodiments, the foot structure includes a label indicating an associated tunnel diameter of the shaft assembly and offset of the foot structure from an engaged bone surface. In some embodiments, the shaft assembly includes an indicia indicating an associated left-side or right-side configuration of the shaft assembly with respect to the handle assembly. In some embodiments, the method further includes freely rotating the shaft assembly relative to the handle assembly prior to securing the shaft assembly to the handle assembly. In some embodiments, the method further includes rotating the shaft assembly relative to the handle assembly in a plurality of keyed detent positions prior to securing the shaft assembly to the handle assembly.

It will be readily apparent to those of ordinary skill in the art that aspects of the above summarized embodiments may be utilized, omitted, and/or combined as desired in a given surgical application, without limitation.

BRIEF DESCRIPTION OF THE DRAWINGS

The present disclosure is illustrated and described with reference to the various drawings, in which like reference numbers are used to denote like assembly components and method steps, as appropriate, and in which.

It will be readily apparent to those of ordinary skill in the art that aspects of the above illustrated embodiments may be utilized, omitted, and/or combined as desired in a given surgical application, without limitation.

DETAILED DESCRIPTION

Again, the present disclosure provides an ACL drill guide assembly for use in an ACL or similar surgical procedure. The drill guide assembly is sterilizable and reusable, and includes an engagement end that includes a tongue structure and serrated teeth that are adapted to securely engage the back of the condyle of the knee or other anatomical structure and provide proper angled orientation for subsequent guide pin/drill placement and use. The shaft of the drill guide assembly is movable/rotatable such that the same drill guide assembly may be used for both left-side and right-side procedures. Labeling is provided on the drill guide assembly for conveniently indicating the associated tunnel diameter and offset from the engaged bone surface. Further, the handle and shaft may be disengaged via a convenient locking mechanism.

Figure 1:
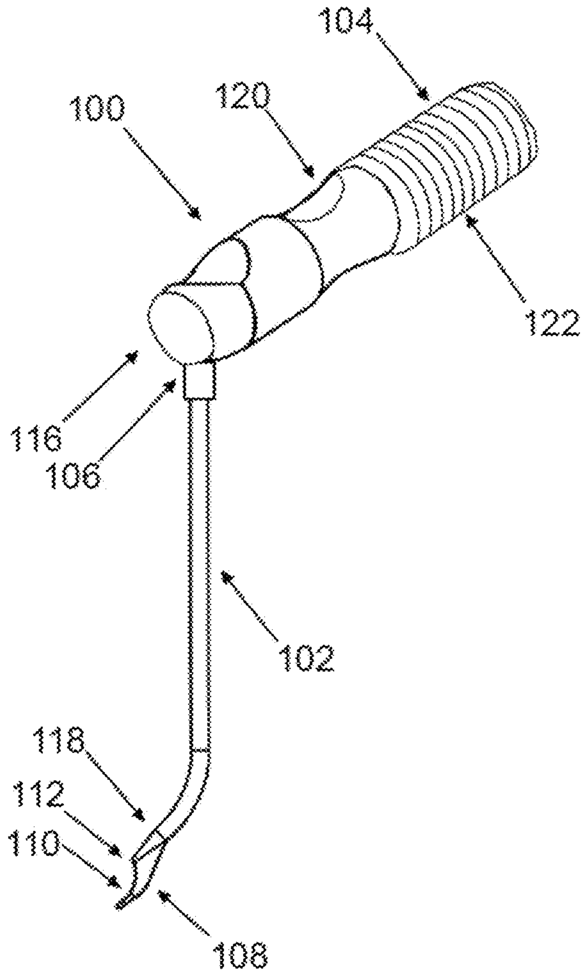
FIG. 1 illustrates a front perspective view of one embodiment of the drill guide assembly of the present disclosure.

FIG. 1 illustrates a front perspective view of one embodiment of the drill guide assembly 100 of the present disclosure. The drill guide assembly 100 includes a shaft assembly 102 that is removably coupled to a handle assembly 104 via a ball seal adapter or the like 106. The shaft assembly 102 includes a cannulated structure or tube through which a guide pin/drill can be removably disposed. The engagement end of the shaft assembly 102 includes a foot structure 108 including a tongue structure 110 and serrated teeth 112 that are adapted to securely engage the back of the condyle of the knee and provide proper angled orientation for subsequent guide pin/drill placement and use through the handle assembly 104 and shaft assembly 102. Labeling 113 is provided on the drill guide assembly 100, in this case on a side or sides of the foot structure 108, for conveniently indicating the associated tunnel diameter and offset from the engaged bone surface. For example, the notation "10" may be used to denote a 10 mm tunnel diameter with a 2 mm offset from the bone engagement surface. The handle assembly 104 and shaft assembly 102 may be disengaged via a convenient locking mechanism 114, in this case via actuation of a locking knob 116. The shaft assembly 102 is movable/rotatable relative to the handle assembly 104 such that the same drill guide assembly 100 may be used for both left-side and right-side procedures. As illustrated, the channel 118 defined by the foot structure 108 is disposed at approximately 45 degrees relative to the shaft assembly 102, and rotated at an angle of approximately 45 degrees relative to the handle assembly 104, although other orientations may be used equally. All of the components illustrated are preferably manufactured from a sterilizable metallic or polymeric material, but may also be made disposable if preferred. The handle assembly 104 may include and number and type of ergonomic recesses 120 and/or surfaces 122 that make the handle assembly 104 easier for a surgeon to handle and manipulate.

Figure 2:
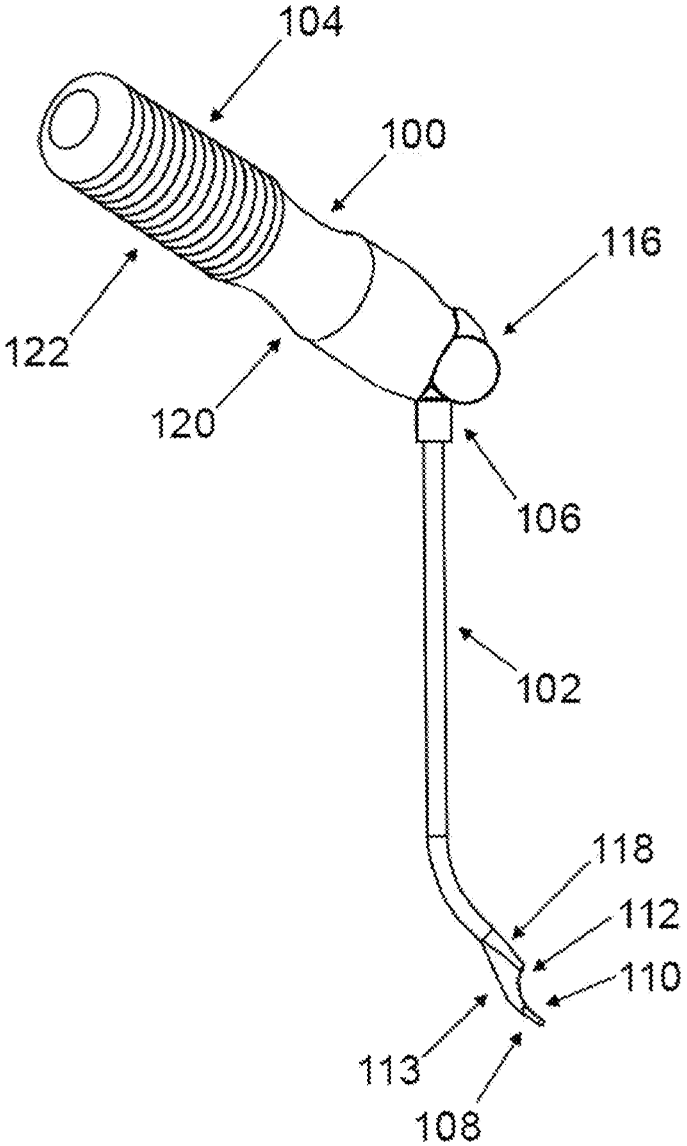
FIG. 2 illustrates a rear perspective view of one embodiment of the drill guide assembly of the present disclosure.

FIG. 2 illustrates a rear perspective view of one embodiment of the drill guide assembly 100 of the present disclosure. Again, the drill guide assembly 100 includes a shaft assembly 102 that is removably coupled to a handle assembly 104 via a ball seal adapter or the like 106. The engagement end of the shaft assembly 102 includes a foot structure 108 including a tongue structure 110 and serrated teeth 112 that are adapted to securely engage the back of the condyle of the knee and provide proper angled orientation for subsequent guide pin/drill placement and use through the handle assembly 104 and shaft assembly 102. Labeling 113 is provided on the drill guide assembly 100, in this case on a side or sides of the foot structure 108, for conveniently indicating the associated tunnel diameter and offset from the engaged bone surface. The handle assembly 104 and shaft assembly 102 may be disengaged via a convenient locking mechanism 114, in this case via actuation of a locking knob 116. The shaft assembly 102 is movable/rotatable relative to the handle assembly 104 such that the same drill guide assembly 100 may be used for both left-side and right-side procedures. As illustrated, the channel 118 defined by the foot structure 108 is disposed at approximately 45 degrees relative to the shaft assembly 102, and rotated at an angle of approximately 45 degrees relative to the handle assembly 104, although other orientations may be used equally. All of the components illustrated are preferably manufactured from a sterilizable metallic or polymeric material, but may also be made disposable if preferred. The handle assembly 104 may include and number and type of ergonomic recesses 120 and/or surfaces 122 that make the handle assembly 104 easier for a surgeon to handle and manipulate.

Figure 3:
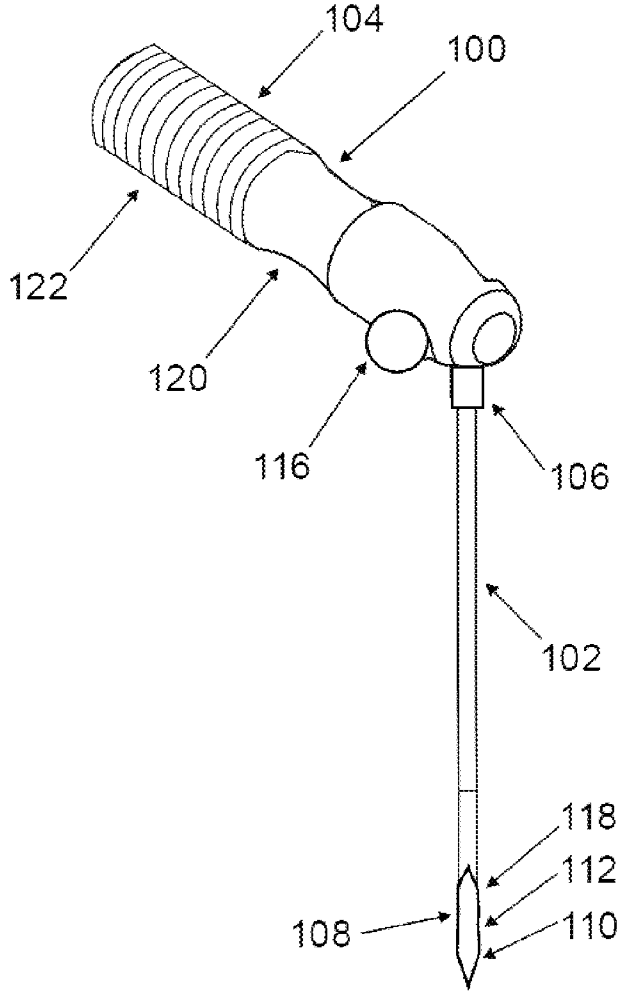
FIG. 3 illustrates another front perspective view of one embodiment of the drill guide assembly of the present disclosure.

FIG. 3 illustrates another front perspective view of one embodiment of the drill guide assembly 100 of the present disclosure. Again, the drill guide assembly 100 includes a shaft assembly 102 that is removably coupled to a handle assembly 104 via a ball seal adapter or the like 106. The engagement end of the shaft assembly 102 includes a foot structure 108 including a tongue structure 110 and serrated teeth 112 that are adapted to securely engage the back of the condyle of the knee and provide proper angled orientation for subsequent guide pin/drill placement and use. Labeling 113 is provided on the drill guide assembly 100, in this case on a side or sides of the foot structure 108, for conveniently indicating the associated tunnel diameter and offset from the engaged bone surface. The handle assembly 104 and shaft assembly 112 may be disengaged via a convenient locking mechanism 114, in this case via actuation of a locking knob 116. The shaft assembly 102 is movable/rotatable relative to the handle assembly 104 such that the same drill guide assembly 100 may be used for both left-side and right-side procedures. As illustrated, the channel 118 defined by the foot structure 108 is disposed at approximately 45 degrees relative to the shaft assembly 102, and rotated at an angle of approximately 45 degrees relative to the handle assembly 104, although other orientations may be used equally. All of the components illustrated are preferably manufactured from a sterilizable metallic or polymeric material, but may also be made disposable if preferred. The handle assembly 104 may include and number and type of ergonomic recesses 120 and/or surfaces 122 that make the handle assembly 104 easier for a surgeon to handle and manipulate.

Figure 4:
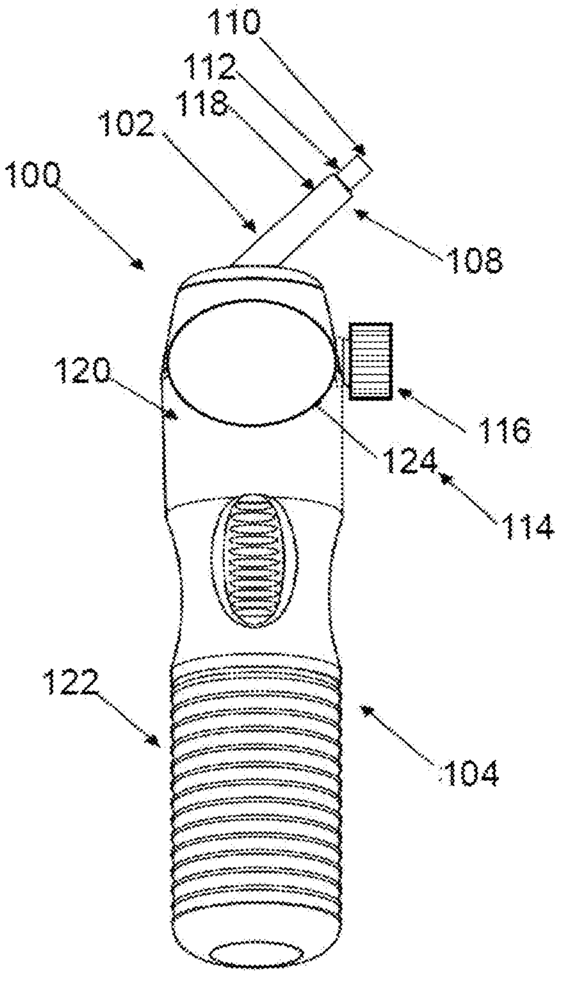
FIG. 4 illustrates a top perspective view of one embodiment of the drill guide assembly of the present disclosure.

FIG. 4 illustrates a top perspective view of one embodiment of the drill guide assembly 100 of the present disclosure. Again, the drill guide assembly 100 includes a shaft assembly 102 that is removably coupled to a handle assembly 104 via a ball seal adapter or the like 106. The engagement end of the shaft assembly 102 includes a foot structure 108 including a tongue structure 110 and serrated teeth 112 that are adapted to securely engage the back of the condyle of the knee and provide proper angled orientation for subsequent guide pin/drill placement and use. Labeling 113 is provided on the drill guide assembly 100, in this case on a side or sides of the foot structure 108, for conveniently indicating the associated tunnel diameter and offset from the engaged bone surface. The handle assembly 104 and shaft assembly 112 may be disengaged via a convenient locking mechanism 114, in this case via actuation of a locking knob 116. The shaft assembly 102 is movable/rotatable relative to the handle assembly 104 such that the same drill guide assembly 100 may be used for both left-side and right-side procedures. As illustrated, the channel 118 defined by the foot structure 108 is disposed at approximately 45 degrees relative to the shaft assembly 102, and rotated at an angle of approximately 45 degrees relative to the handle assembly 104, although other orientations may be used equally. All of the components illustrated are preferably manufactured from a sterilizable metallic or polymeric material, but may also be made disposable if preferred. The handle assembly 104 may include and number and type of ergonomic recesses 120 and/or surfaces 122 that make the handle assembly 104 easier for a surgeon to handle and manipulate. In FIG. 4, the port 24 of the handle assembly 104 is visible, via which the guide pin/drill can be disposed through the handle assembly 104 and shaft assembly 102 after the foot structure 108 is securely engaged with the back of the condyle of the knee.

Figure 5:
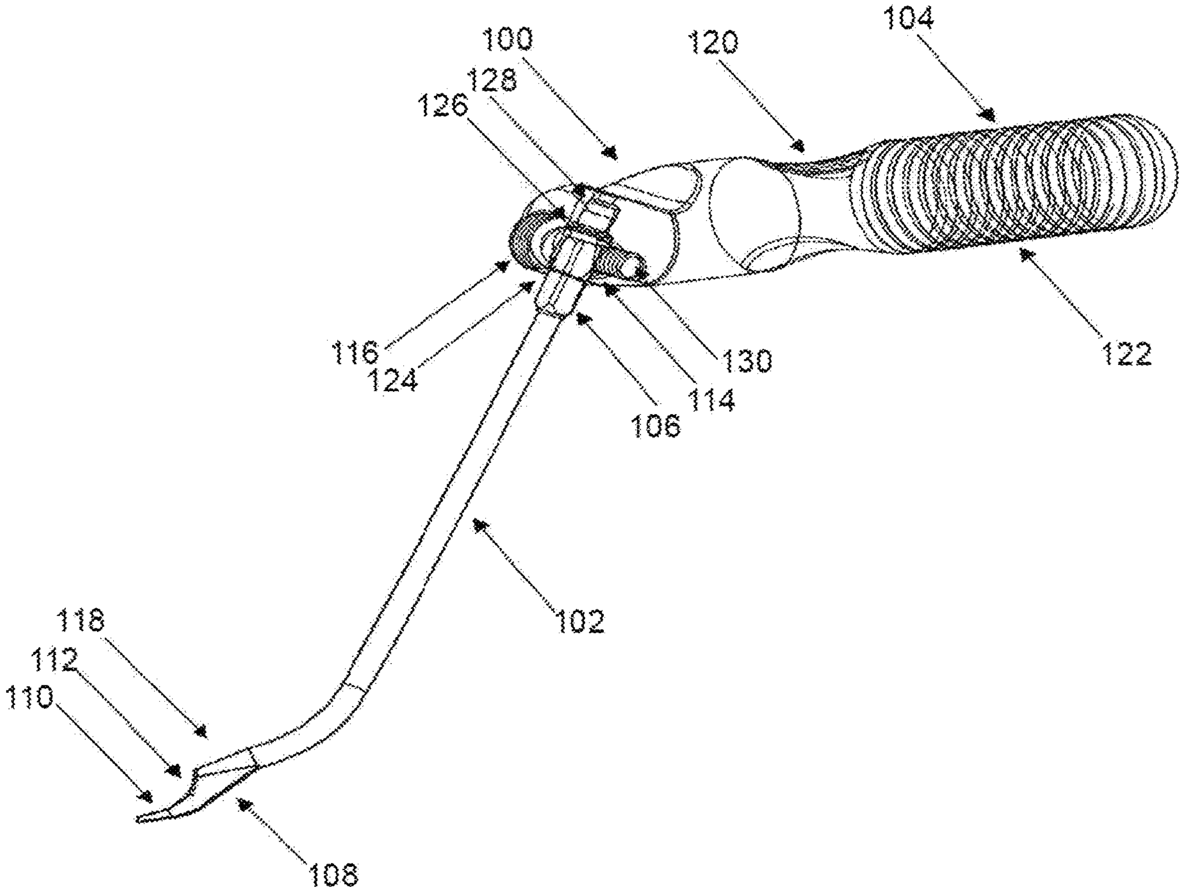
FIG. 5 illustrates a semi-transparent front perspective view of one embodiment of the drill guide assembly of the present disclosure.

FIG. 5 illustrates a semi-transparent front perspective view of one embodiment of the drill guide assembly 100 of the present disclosure. As illustrated, the drill guide assembly 100 includes a shaft assembly 102 that is removably coupled to a handle assembly 104 via a ball seal adapter or the like 106 that is disposed within a port 124 provided at the end of the handle assembly 104. The handle assembly 104 and shaft assembly 102 may be disengaged via a convenient locking mechanism 114, in this case via actuation of a locking knob 116. The shaft assembly 102 is movable/rotatable relative to the handle assembly 104 such that the same drill guide assembly may be used for both left-side and right-side procedures. As illustrated, the locking mechanism 114 that secured the ball seal adapter 106 of the shaft assembly 102 that is disposed in the port 124 provided at the end of the handle assembly 104 includes a ball seal 126 through which an end portion 128 of the shaft assembly is concentrically disposed. A constriction screw 130 coupled to the locking knob 116 is rotated to draw structures of the handle assembly 104 together to secure the shaft assembly 102 and the handle assembly 104 together and prevent relative rotation once is a desired alignment. A retaining pin 132 is used to secure the locking mechanism 114 within the handle assembly 104.

Figure 6:
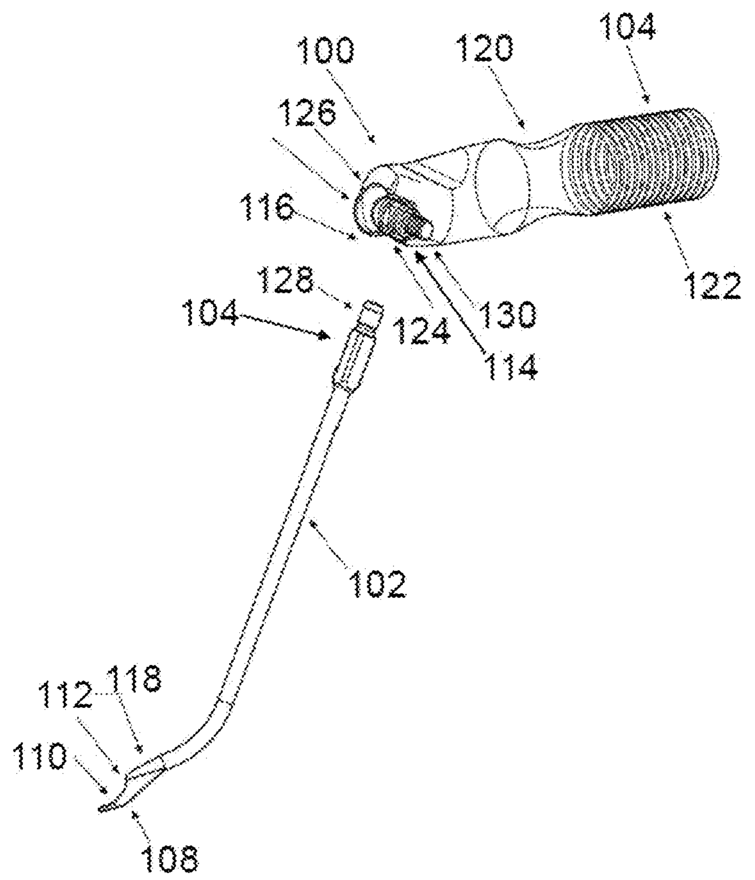
FIG. 6 illustrates an exploded semi-transparent front perspective view of one embodiment of the drill guide assembly of the present disclosure.

FIG. 6 illustrates an exploded semi-transparent front perspective view of one embodiment of the drill guide assembly 100 of the present disclosure. Again, as illustrated, the drill guide assembly 100 includes a shaft assembly 102 that is removably coupled to a handle assembly 104 via a ball seal adapter or the like 106 that is disposed within a port 124 provided at the end of the handle assembly 104. The handle assembly 104 and shaft assembly 102 may be disengaged via a convenient locking mechanism 114, in this case via actuation of a locking knob 116. The shaft assembly 102 is movable/rotatable relative to the handle assembly 104 such that the same drill guide assembly may be used for both left-side and right-side procedures. As illustrated, the locking mechanism 114 that secured the ball seal adapter 106 of the shaft assembly 102 that is disposed in the port 124 provided at the end of the handle assembly 104 includes a ball seal 126 through which an end portion 128 of the shaft assembly is concentrically disposed. A constriction screw 130 coupled to the locking knob 116 is rotated to draw structures of the handle assembly 104 together to secure the shaft assembly 102 and the handle assembly 104 together and prevent relative rotation once is a desired alignment. A retaining pin 132 is used to secure the locking mechanism 114 within the handle assembly 104.

Figure 7:
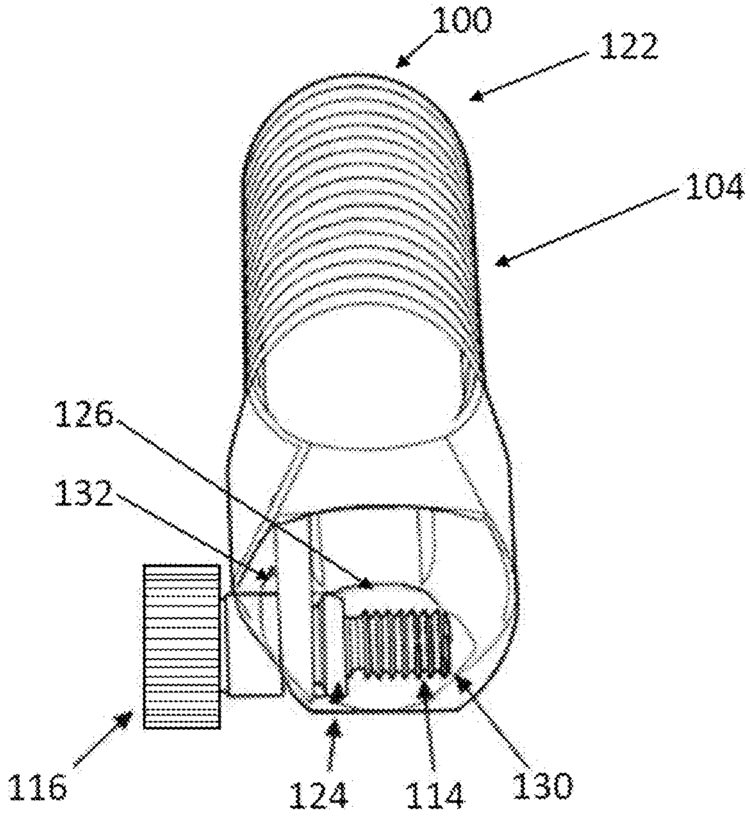
FIG. 7 illustrates a partial semi-transparent top perspective view of one embodiment of the drill guide assembly of the present disclosure, highlighting the associated locking mechanism.

FIG. 7 illustrates a partial semi-transparent top perspective view of one embodiment of the drill guide assembly 100 of the present disclosure, highlighting the associated locking mechanism 114. As illustrated, the ball seal adapter 106 at the end of the shaft assembly 102 includes an insertion fitting 128 that is disposed in the port 124 at the end of the handle assembly 104 and through a ball seal 126 disposed within the handle assembly 104. The locking knob 116 and constriction screw 130 are threaded into the handle assembly 104 perpendicular to the shaft assembly 102 and include a shoulder structure that compress the ball seal 126 into the ball seal adapter 106, thereby locking the shaft assembly 102 into the handle assembly 104 and preventing relative movement and rotation. A retaining pin 132 disposed in the handle assembly 104 crosses the locking knob 116 and rests in a recess manufactured into the locking knob 116, thereby securing the locking knob 116 to the handle assembly 104 such that the locking knob 116 may not be backed completely out of the handle assembly 104 when rotated on the threads. It will be readily apparent to those of ordinary skill in the art that other locking mechanisms 114 may be used equally, provided that the shaft assembly 102 is rotatable and removable, and subsequently securable, with respect to the handle assembly 104. Alternatively, the ball seal adapter 106 and port 124 may be keyed, such that the shaft assembly 102 is only removable with respect to the handle assembly 104, but may not be rotated between available left-side and right-side configurations.

Figure 8:
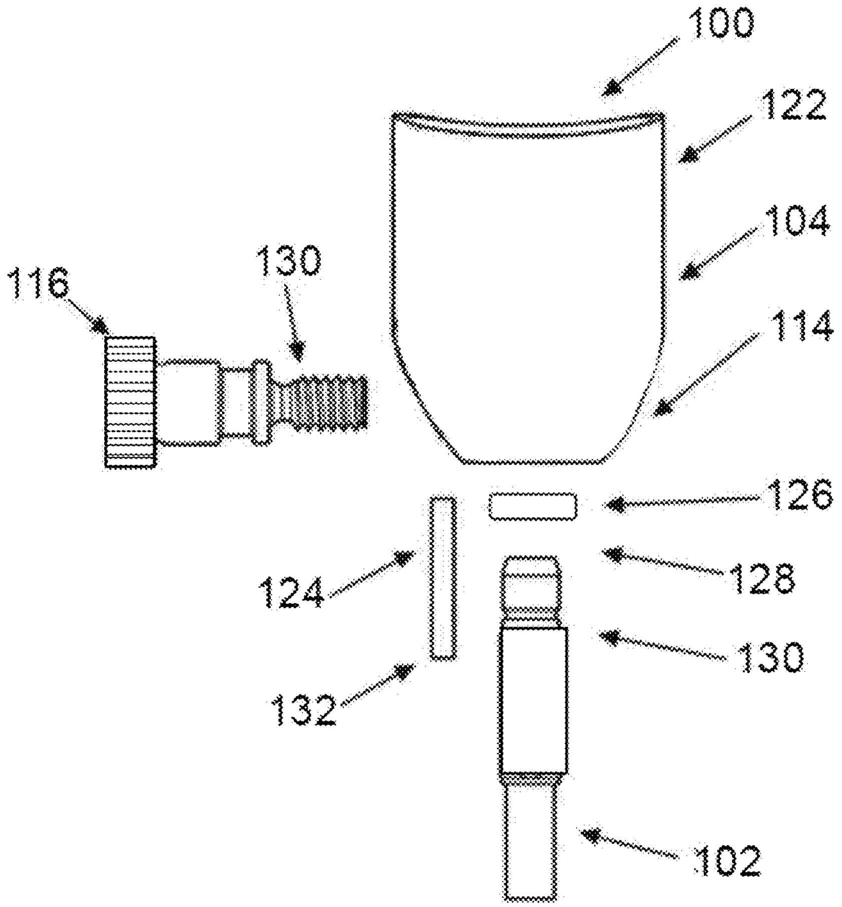
FIG. 8 illustrates a partial exploded semi-transparent top perspective view of one embodiment of the drill guide assembly of the present disclosure, highlighting the associated locking mechanism.

FIG. 8 illustrates a partial exploded semi-transparent top perspective view of one embodiment of the drill guide assembly 100 of the present disclosure, highlighting the associated locking mechanism 114. Again, as illustrated, the ball seal adapter 106 at the end of the shaft assembly 102 includes an insertion fitting 128 that is disposed in the port 124 at the end of the handle assembly 104 and through a ball seal 126 disposed within the handle assembly 104. The locking knob 116 and constriction screw 130 are threaded into the handle assembly 104 perpendicular to the shaft assembly 102 and include a shoulder structure that compress the ball seal 126 into the ball seal adapter 106, thereby locking the shaft assembly 102 into the handle assembly 104 and preventing relative movement and rotation. A retaining pin 132 disposed in the handle assembly 104 crosses the locking knob 116 and rests in a recess manufactured into the locking knob 116, thereby securing the locking knob 116 to the handle assembly 104 such that the locking knob 116 may not be backed completely out of the handle assembly 104 when rotated on the threads. It will be readily apparent to those of ordinary skill in the art that other locking mechanisms 114 may be used equally, provided that the shaft assembly 102 is rotatable and removable, and subsequently securable, with respect to the handle assembly 104. Alternatively, the ball seal adapter 106 and port 124 may be keyed, such that the shaft assembly 102 is only removable with respect to the handle assembly 104, but may not be rotated between available left-side and right-side configurations.

In all embodiments, the shaft assembly 102 is a cannulated structure and the foot structure 108 is a more prismatic structure with the protruding tongue structure 110 and serrated teeth 112 adapted to find and engage the back of the condyle. The foot structure 108 defines a channel 118 that is adapted to conduit the guide pin/drill to the bone site.

Figure 9:
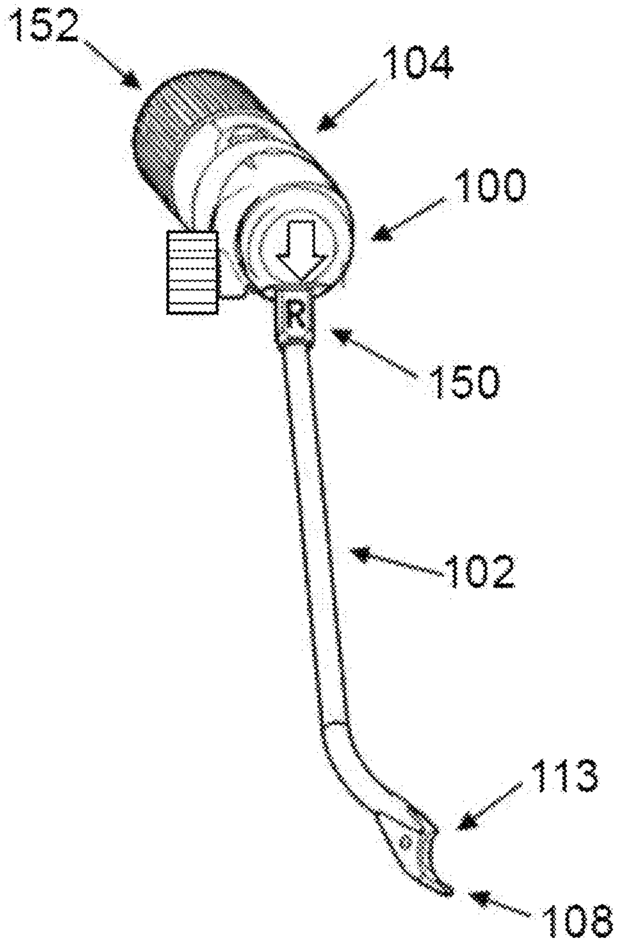
FIG. 9 illustrates a front perspective view of another embodiment of the drill guide assembly of the present disclosure.

FIG. 9 illustrates a front perspective view of another embodiment of the drill guide assembly 100 of the present disclosure. As illustrated, the end of the shaft assembly 102 near the handle assembly 104 may include indicia 150 indicating that the shaft assembly 102 is disposed in a left-side (L) or right-side (R) configuration with respect to the handle assembly 104, depending on whether the L or R is lined up with the associated marking (e.g., arrow) on the handle assembly 104, for example. Thus, the shaft assembly 102 may be reversible, and usable in both left-side and right-side procedures depending on how it is rotated relative to the handle assembly 104. Labeling 113 may again be provided on the drill guide assembly 100, in this case on a side or sides of the foot structure 108, for conveniently indicating the associated tunnel diameter and offset from the engaged bone surface. These markings all serve to reduce and eliminate possible guide pin placement/drilling errors during a procedure. Here, a recessed area 152 surrounding the guide port 124 is also provided in the handle assembly 104 to aide in shaft assembly advancement and guide pin/drill engagement.

Figure 10:
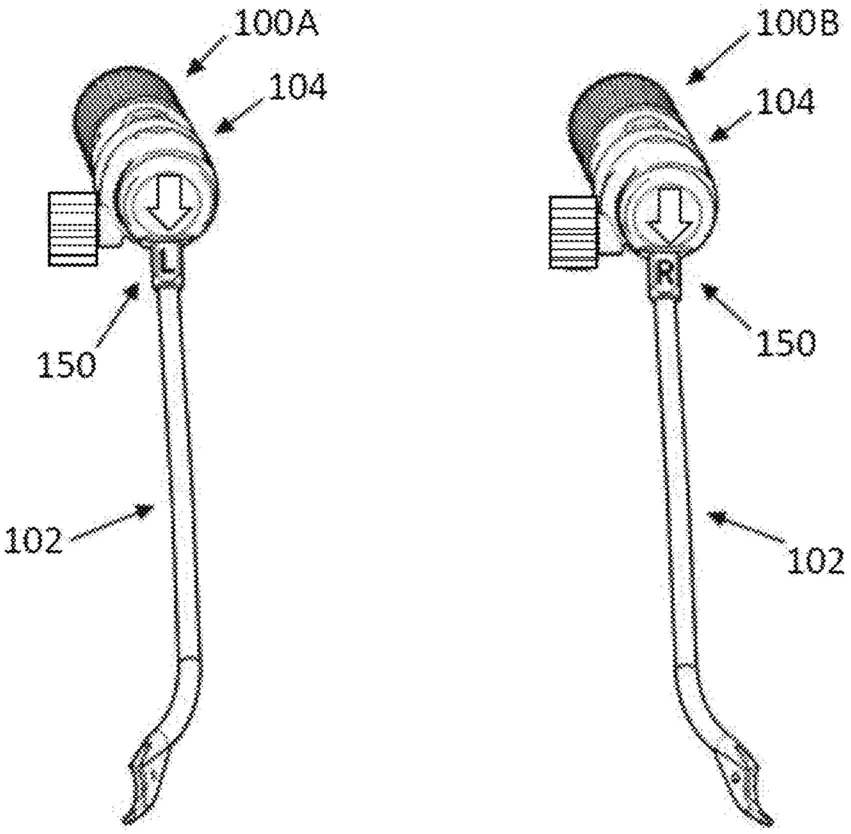
FIG. 10 illustrates a front perspective view of another embodiment of the drill guide assembly of the present disclosure, highlighting left and right configurations.

FIG. 10 illustrates a front perspective view of another embodiment of the drill guide assembly of the present disclosure, highlighting left and right configurations 100*a*, 100*b* as denoted by the L and R indicia 150 alignment with the arrow on the handle assembly 104.

Figure 11:
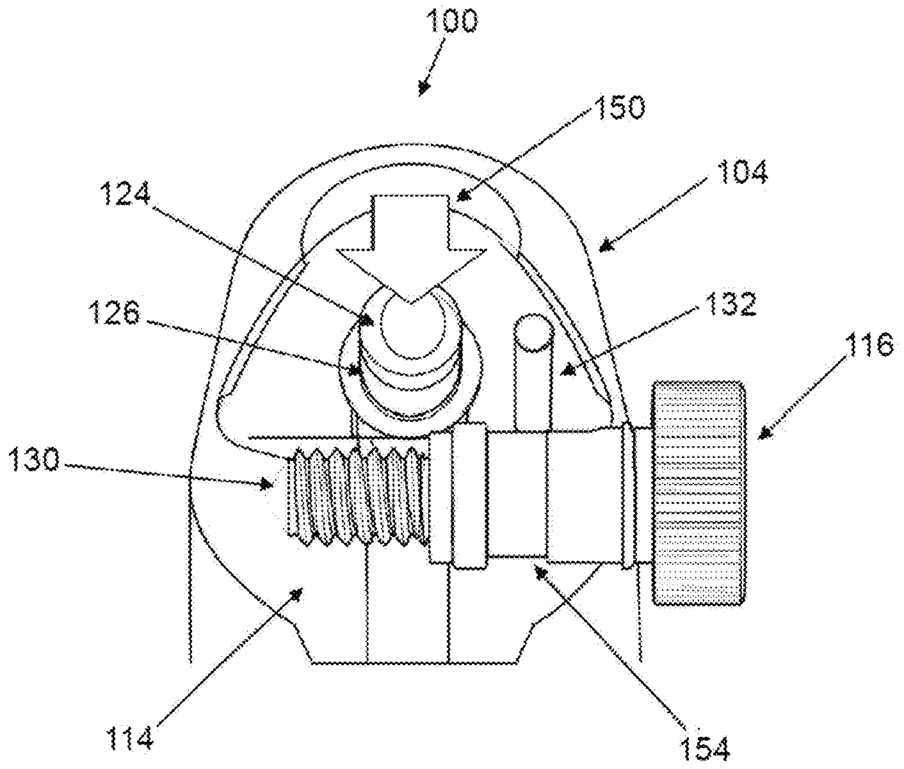
FIG. 11 illustrates a partial semi-transparent top perspective view of another embodiment of the drill guide assembly of the present disclosure, highlighting the associated locking mechanism.

FIG. 11 illustrates a partial semi-transparent top perspective view of another embodiment of the drill guide assembly 100 of the present disclosure, highlighting the associated locking mechanism 114. As illustrated, the ball seal adapter 106 at the end of the shaft assembly 102 includes an insertion fitting 128 that is disposed in the port 124 at the end of the handle assembly 104 and through a ball seal spring 126 disposed within the handle assembly 104. The locking knob 116 and constriction screw 130 are threaded into the handle assembly 104 perpendicular to the shaft assembly 102 and include a shoulder structure that compress the ball seal spring 126 into the ball seal adapter 106, thereby locking the shaft assembly 102 into the handle assembly 104 and preventing relative movement and rotation. A retaining pin 132 disposed in the handle assembly 104 crosses the locking knob 116 and rests in a recess 154 manufactured into the locking knob 116, thereby securing the locking knob 116 to the handle assembly 104 such that the locking knob 116 may not be backed completely out of the handle assembly 104 when rotated on the threads. It will be readily apparent to those of ordinary skill in the art that other locking mechanisms 114 may be used equally, provided that the shaft assembly 102 is rotatable and removable, and subsequently securable, with respect to the handle assembly 104. Alternatively, the ball seal adapter 106 and port 124 may be keyed, such that the shaft assembly 102 is only removable with respect to the handle assembly 104, but may not be rotated between available left-side and right-side configurations.

Figure 12:
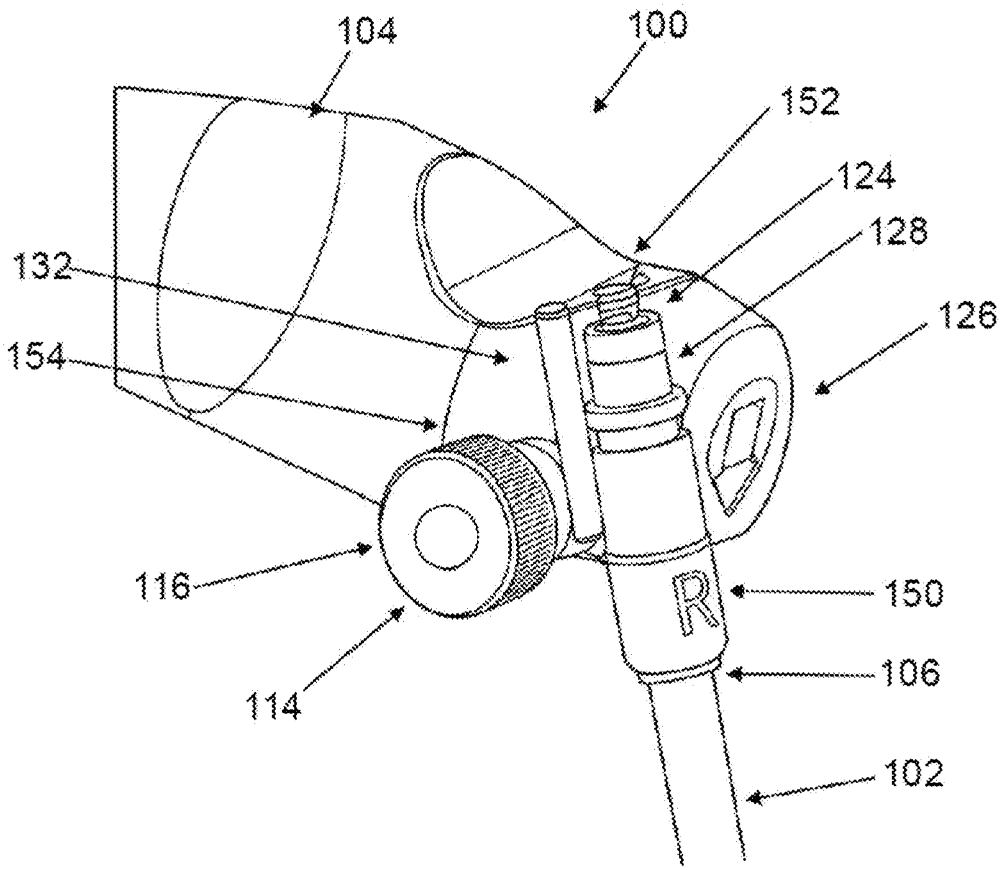
FIG. 12 illustrates a partial semi-transparent front perspective view of another embodiment of the drill guide assembly of the present disclosure, highlighting the associated locking mechanism.

FIG. 12 illustrates a partial semi-transparent front perspective view of another embodiment of the drill guide assembly 100 of the present disclosure, highlighting the associated locking mechanism 114. Again, as illustrated, the ball seal adapter 106 at the end of the shaft assembly 102 includes an insertion fitting 128 that is disposed in the port 124 at the end of the handle assembly 104 and through a ball seal spring 126 disposed within the handle assembly 104. The locking knob 116 and constriction screw 130 are threaded into the handle assembly 104 perpendicular to the shaft assembly 102 and include a shoulder structure that compress the ball seal spring 126 into the ball seal adapter 106, thereby locking the shaft assembly 102 into the handle assembly 104 and preventing relative movement and rotation. A retaining pin 132 disposed in the handle assembly 104 crosses the locking knob 116 and rests in a recess 154 manufactured into the locking knob 116, thereby securing the locking knob 116 to the handle assembly 104 such that the locking knob 116 may not be backed completely out of the handle assembly 104 when rotated on the threads. It will be readily apparent to those of ordinary skill in the art that other locking mechanisms 114 may be used equally, provided that the shaft assembly 102 is rotatable and removable, and subsequently securable, with respect to the handle assembly 104. Alternatively, the ball seal adapter 106 and port 124 may be keyed, such that the shaft assembly 102 is only removable with respect to the handle assembly 104, but may not be rotated between available left-side and right-side configurations.

Figure 13:
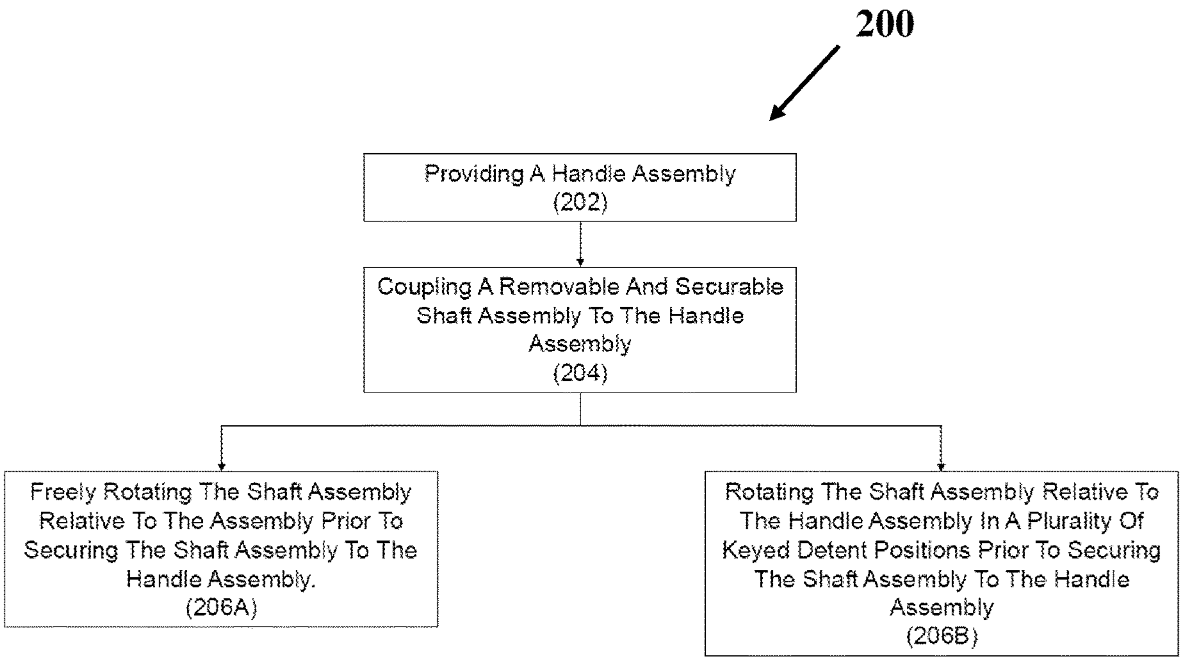
FIG. 13 illustrates one embodiment of the drill guide method of the present disclosure.

FIG. 13 illustrates one embodiment of the drill guide method 200 of the present disclosure. The method 200 includes providing a handle assembly (step 202) and coupling a removable and securable shaft assembly to the handle assembly (step 204), where the shaft assembly includes a foot structure including a tongue structure and serrated teeth that are adapted to securely engage a back of a condyle of a knee of a patient and provide proper angled orientation for subsequent guide pin/drill placement and use through the handle assembly and shaft assembly. A channel defined by the foot structure is disposed at an inclination angle relative to the shaft assembly. The channel defined by the foot structure is disposed at a left-side or right-side rotation angle relative to the handle assembly. The foot structure includes a label indicating an associated tunnel diameter of the shaft assembly and offset of the foot structure from an engaged bone surface. The shaft assembly and handle assembly also include indicia indicating an associated left-side or right-side configuration of the shaft assembly with respect to the handle assembly. The method 200 also includes freely rotating the shaft assembly relative to the handle assembly prior to securing the shaft assembly to the handle assembly (step 206*a*) or rotating the shaft assembly relative to the handle assembly in a plurality of keyed detent positions prior to securing the shaft assembly to the handle assembly (step 206*b*).

Although the present disclosure is illustrated and described with reference to illustrative embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following non-limiting claims for all purposes.

What is claimed is:

1. A drill guide assembly, comprising:

a handle assembly comprising a distal portion defining a housing and a proximal portion having a plurality of ergonomic surfaces and recesses; and a shaft assembly removably and securably coupled to the distal portion of the handle assembly and rotatable relative thereto, wherein the shaft assembly is reversible and useable in both left-side and right-side procedures based on its position relative to the handle assembly, wherein the shaft assembly comprises a cannulated tube comprising a curved distal engagement end and a proximal end, wherein the curved distal engagement end comprises a tapered foot structure comprising a tongue structure and serrated teeth that are adapted to securely engage a back of a condyle of a knee of a patient and provide proper angled orientation for subsequent guide pin/drill placement and use through the handle assembly and the shaft assembly, wherein the proximal end comprises an indicia indicating an associated left-side or right-side configuration of the shaft assembly with respect to the handle assembly, wherein a channel defined by the foot structure is disposed at an inclination angle relative to the shaft assembly and is adapted to conduit the guide pin/drill placement at the inclination angle relative to the shaft assembly, wherein the foot structure comprises a label indicating an offset of the foot structure from an engaged bone surface of the patient; and wherein the housing of the distal portion of the handle assembly comprises a locking knob, a constriction screw, a retaining pin, and a spring seal and the proximal end of the shaft assembly comprises a spring seal adapter by which the shaft assembly securably couples to the handle assembly to prevent relative rotation between the handle assembly and the shaft assembly once in a desired alignment.

2. The drill guide assembly of claim 1, wherein the channel defined by the foot structure is disposed at a left-side or right-side rotation angle relative to the handle assembly and is adapted to conduit the guide pin/drill placement at the left-side or right-side rotation angle relative to the handle assembly.

3. The drill guide assembly of claim 1, wherein the foot structure comprises a label indicating an associated tunnel diameter of the shaft assembly.

4. The drill guide assembly of claim 1, wherein the shaft assembly is freely rotatable relative to the handle assembly prior to being secured to the handle assembly.

5. The drill guide assembly of claim 1, wherein the shaft assembly is rotatable relative to the handle assembly in a plurality of keyed detent positions prior to being secured to the handle assembly.

6. A drill guide method, comprising:

providing a drill guide assembly as stated in claim 1; and coupling the proximal end of the removable and securable shaft assembly to the housing of the distal portion of the handle assembly in a left-side or right-side configuration based on a desired alignment and securing the shaft assembly and the handle assembly together once in the desired alignment, preventing relative rotation between the handle assembly and the shaft assembly;

engaging the foot structure of the shaft assembly with the back of the condyle of the knee of the patient;

and inserting a guide pin or drill through the handle assembly and the shaft assembly to a bone site of the patient.

7. The drill guide method of claim 6, wherein the channel defined by the foot structure is disposed at a left-side or right-side rotation angle relative to the handle assembly and is adapted to conduit the guide pin/drill placement at the left-side or right-side rotation angle relative to the handle assembly.

8. The drill guide method of claim 6, wherein the foot structure comprises a label indicating an associated tunnel diameter of the shaft assembly.

9. The drill guide method of claim 6, further comprising freely rotating the shaft assembly relative to the handle assembly prior to securing the shaft assembly to the handle assembly.

10. The drill guide method of claim 6, further comprising rotating the shaft assembly relative to the handle assembly in a plurality of keyed detent positions prior to securing the shaft assembly to the handle assembly.

* * * * *